US005853758A

United States Patent [19]

Lo

[11] Patent Number: 5,853,758
[45] Date of Patent: Dec. 29, 1998

[54] PREPARATION OF TABLETS OF INCREASED STRENGTH

[75] Inventor: Julian Belknap Lo, Old Lyme, Conn.

[73] Assignee: Pfizer Inc., New York, N.Y.

[21] Appl. No.: 677,992

[22] Filed: Jul. 10, 1996

Related U.S. Application Data

[63] Continuation of Ser. No. 256,296, Jul. 13, 1994, abandoned, which is a continuation of Ser. No. 819,553, Jan. 13, 1992, abandoned.

[51] Int. Cl.$^6$ ..................................................... A61K 9/20
[52] U.S. Cl. ......................... 424/464; 424/465; 514/960; 514/961
[58] Field of Search ................................. 424/464, 465; 514/960, 961

[56] References Cited

U.S. PATENT DOCUMENTS

| | | | |
|---|---|---|---|
| 2,987,445 | 6/1961 | Levesque | 264/122 |
| 3,432,592 | 3/1969 | Speiser | 424/19 |
| 3,487,138 | 12/1969 | Hess | 264/112 |
| 3,653,914 | 4/1972 | Schmitt | 99/78 |
| 3,885,026 | 5/1975 | Heinemann et al. | 424/14 |
| 3,923,939 | 12/1975 | Baker | 264/49 |
| 3,961,004 | 6/1976 | Nasir | 264/115 |
| 4,036,948 | 7/1977 | Kitamori | 424/32 |
| 4,132,753 | 1/1979 | Blichare | 264/25 |
| 4,134,943 | 1/1979 | Knitsch | 264/49 |
| 4,166,107 | 8/1979 | Miller | 424/19 |
| 4,305,502 | 12/1981 | Gregory | 206/532 |
| 4,760,094 | 7/1988 | Blank | 514/629 |
| 4,957,681 | 9/1990 | Klimesch | 264/211.23 |
| 4,994,227 | 2/1991 | Dietz | 264/328.16 |
| 5,036,097 | 7/1991 | Floyd | 514/400 |
| 5,137,669 | 8/1992 | Leonard | 264/120 |

FOREIGN PATENT DOCUMENTS

| | | |
|---|---|---|
| 1137156 | 12/1968 | United Kingdom . |
| 1341515 | 12/1973 | United Kingdom . |
| 1422768 | 1/1976 | United Kingdom . |
| 9211845 | 7/1992 | WIPO . |

OTHER PUBLICATIONS

Remington's Pharmaceutical Science, 18th Edition, pp. 1633–1639 (1990).

Wells et al., J. Pharm. Pharmacol., 46P (1982).

Gordon et al., J. Pharm. Sci., 79 (1), 43 (1990).

Primary Examiner—Thurman K. Page
Assistant Examiner—James M. Spear
Attorney, Agent, or Firm—Peter C. Richardson; Paul H. Ginsburg; Grover F. Fuller, Jr.

[57] ABSTRACT

Tablets of increased strength are manufactured by combining and compressing a meltable binder, excipients and a pharmaceutically active agent into a tablet, melting the binder in the tablet, and then solidifying the binder.

7 Claims, 2 Drawing Sheets

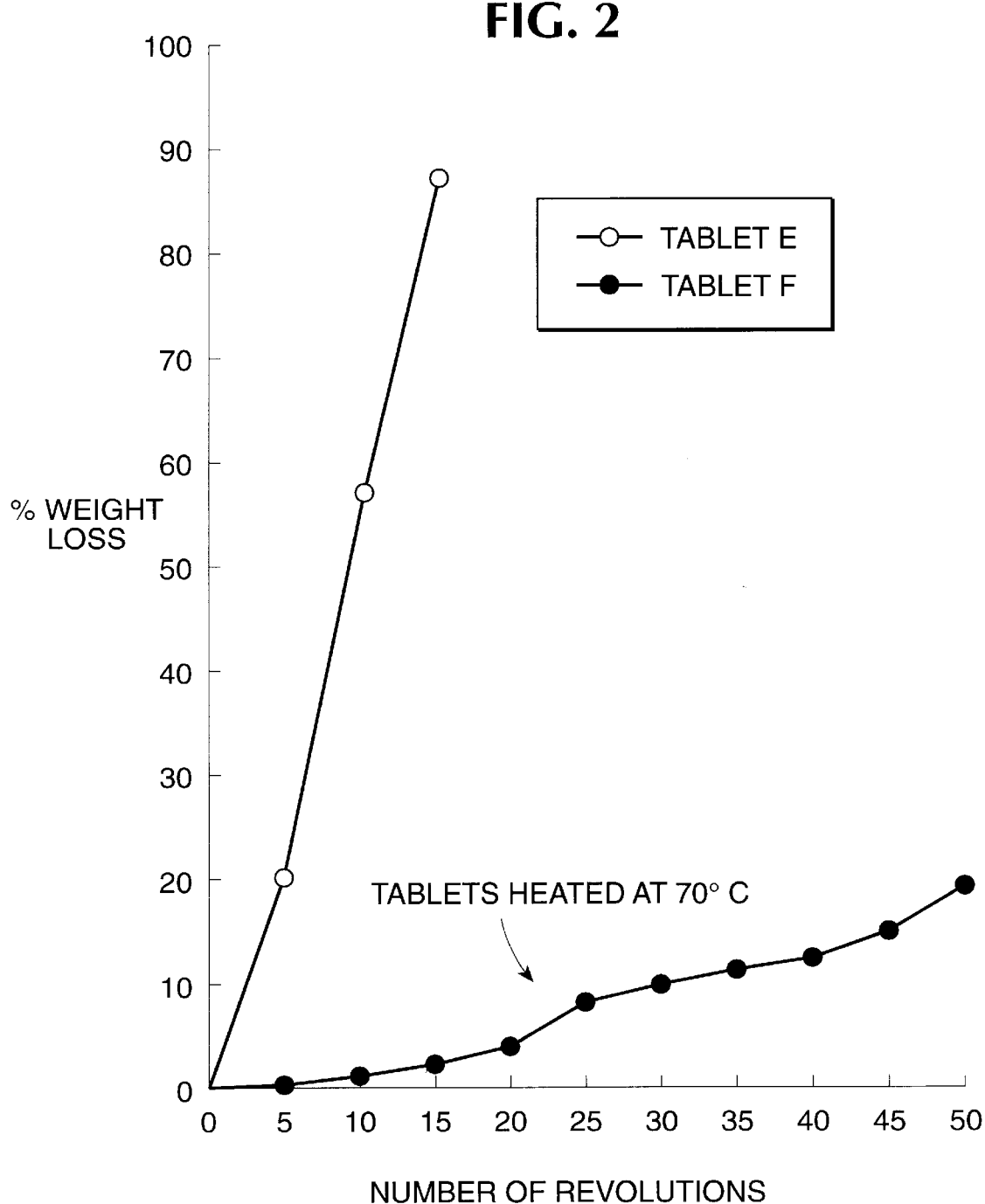

PREPARATION OF TABLETS OF INCREASED STRENGTH

This is a continuation of application Ser. No. 08/256,296, filed on Jul. 13, 1994, abandoned which is the national phase of PCT Application No. PCT/US92/07497, filed Sep. 10, 1992, which, in turn, was a continuation of Ser. No. 07/819,553, filed Jan. 13, 1992, now abandoned.

This invention relates to a method for the preparation of a tablet of increased strength, and to tablets when made by said method. The method is particularly useful in the manufacture of tablets, that contain pharmaceutically active agents which are difficult to compress; that are soft and chewable; and that are fast-disintegrating and porous.

Pharmaceuticals are often administered orally in the form of a tablet. The tablet is usually manufactured by combining tablet ingredients and compressing the combined ingredients in a mold. Due to the compression, tablets of mechanical stability are formed capable of withstanding disintegration during handling including removal from the mold, packing and transport. Mechanical stability depends on many factors, one of which is the compressibility of the pharmaceutically active agent in the tablet, particularly when large amounts of the agent are contained in a single tablet, and another one of which is the porosity of the tablet.

The porosity of a tablet relates to ease of tablet disintegration not only during handling but also during administration whether orally or rectally, and whether disintegration takes place in the mouth, or in the stomach. An increase in the disintegration rate in the mouth facilitates administration to patients in general, and to the very young, the elderly, and non-human animals, in particular. Administration is also facilitated by use of soft chewable tablets. Since such tablets are soft, having a hardness of less than about 6 kp, tablet friability is often a problem.

Tablets of increased porosity and disintegration rates are disclosed in U.S. Pat. Nos. 3,885,026, 4,134,943 and 4,305,502. These patents suggest various ways of dealing with the problems associated with the handling of such highly porous tablets. U.S. Pat. No. 4,305,502 suggests reducing the amount of handling of the tablets by forming them in situ in a substrate having depressions for deposition of tablets. However, removal of tablets from these depressions is more difficult than simple removal from a bottle or tube.

U.S. Pat. Nos. 3,885,026 and 4,134,943 suggest increasing tablet strength of porous tablets by first compressing the tablet and then volatilizing a readily volatilizable solid adjuvant incorporated in the tablet to attain desired porosity. The maximum porosity obtained according to U.S. Pat. No. 3,885,026 is 50% and preferably 10 to 30%.

French patent 2,231,365 and Belgian patent 668121 disclose water insoluble meltable binders used in the manufacture of sustained release tablets.

The invention provides a method for the preparation of a tablet of increased strength by including the steps of (a) combining and compressing a meltable binder, at least one excipient, and a pharmaceutically active agent into a tablet, (b) melting said binder in said tablet, and (c) solidifying said binder.

BRIEF DESCRIPTION OF THE DRAWINGS

FIG. 2 shows a friability comparison between Tablet F according to the invention and comparison Tablet E.

Figure 1A:
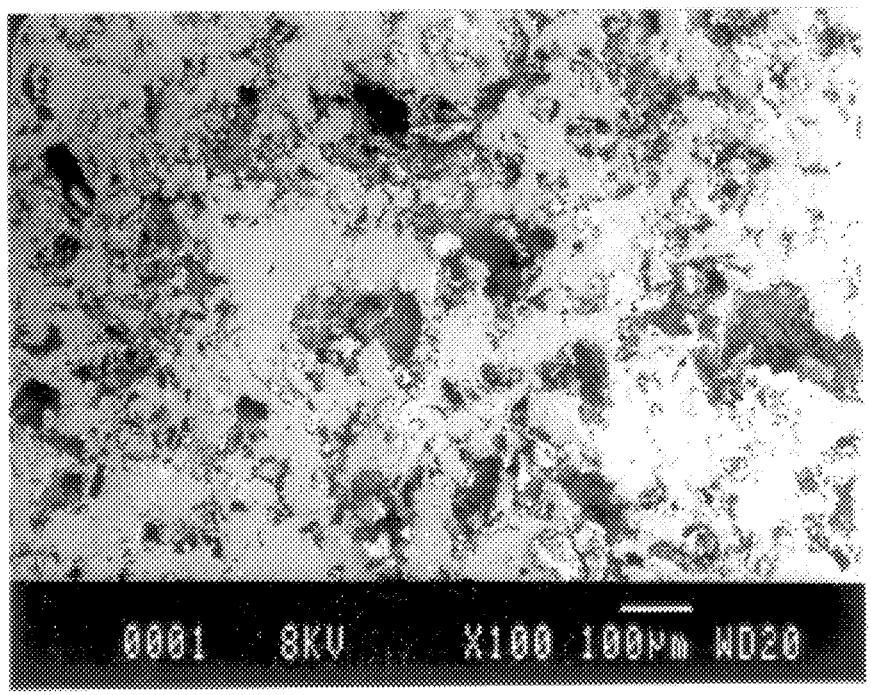
FIG. 1A shows a surface view of comparison Tablet C in Example 2 under a scanning electron microscope at 100× magnification.
Figure 1B:
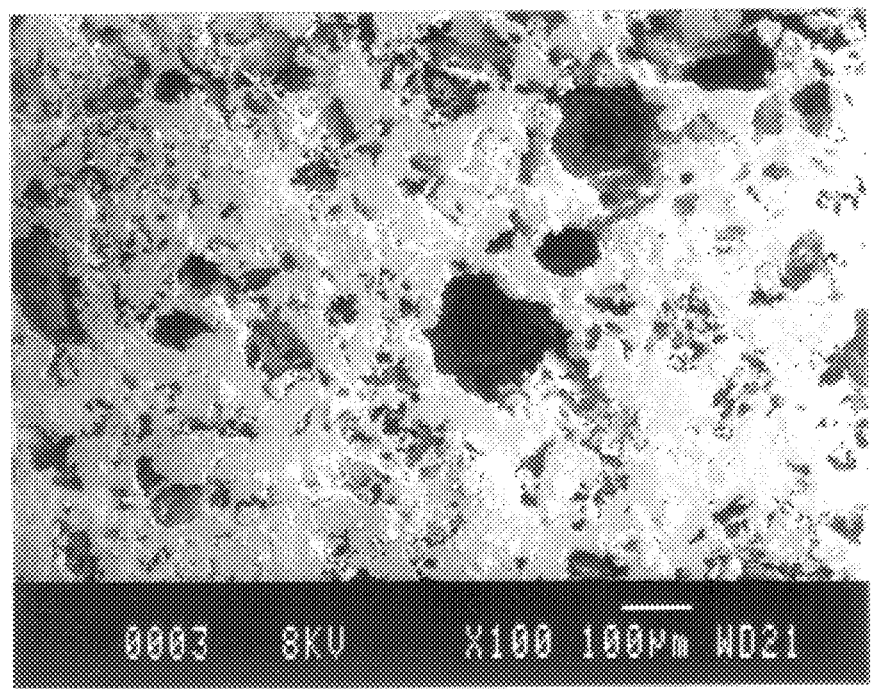
FIG. 1B shows a surface view of Tablet D of the invention in Example 2 under a scanning electron microscope at 100×magnification.

In the context of the invention, a tablet of increased strength refers to a tablet having a higher tablet strength than one made by blending the same tablet ingredients followed by compressing in a conventional tablet compressor.

The tablet ingredients of use in the present invention include a meltable binder, at least one excipient, and a pharmaceutically active agent.

The meltable binder increases the strength of the final tablet when processed according to the method of the invention. The binder has a melting point generally ranging from about 20° C. to about 100° C., preferably from about 40° C. to about 70° C. The melting point of the binder is usually at least about 20° C. since the mixing of the ingredients is usually carried out at about 20° C. and the binder is solid at the mixing temperature. Of course, if mixing is carried out at lower temperatures, a lower melting binder may be used which is solid at that temperature.

The melting point of the binder is usually not higher than about 100° C. since the melting of the binder should be at a temperature at which the activity of the pharmaceutically active agent is not adversely affected. For instance, the melting of the binder should be at a temperature lower than the decomposition temperature of the pharmaceutically active agent as well as any one of the excipients present.

The amount of the meltable binder in the tablet ranges from about 5% to about 40% by weight, preferably from about 8% to about 25% by weight, based on the weight of the tablet. The specific amount depends on several factors, e.g., on use of excessive amounts of the meltable binder the tablet may deform during melting whereas on use of insufficient amounts the desired increase in strength may not be attained.

The meltable binders of the invention may be nonwater-soluble or water soluble. Suitable nonwatersoluble meltable binders include natural fats such as cocoa butter, monoglycerides such as 1-monolaurin (m.p. 63° C.), 2-monolaurin (m.p. 51° C.), 1-monopalmitin (m.p. 77° C.), and 2-monopalmitin (m.p. 68.5° C.), diglycerides such as 1,2-dipalmitin (m.p. 63.5° C.), 1,3-dipalmitin (m.p. 74° C.), 1,2-distearin (m.p. 71° C.), 1,3-distearin (m.p. 80° C.) and 1,3-dioleostearin (m.p. 49° C.), triglycerides such as tripalmitin (m.p. 56° C.) and trimyristin (m.p. 46.5° C.), ethoxylated-fatty esters such as polyethylene (12) distearate and polyoxyethylene (20) sorbitan tristearate, and natural waxes such as carnauba wax (m.p. 83°–86° C.), beeswax (m.p. 62° C.), and paraffins (m.p. 52°–74° C.). Suitable water soluble meltable binders of use in the invention include polyethylene glycols (PEG) having molecular weights ranging from about 1,500 to about 20,000 such as PEG 3350 (m.p. 580° C.) and PEG 8000 (m.p. 62° C.), sucrose esters such as sucrose monostearate (m.p. 49°–56° C.), and sucrose monopalmitate (m.p. 40°–48° C.), ethoxylated fatty acids such as polyoxyethylene (40) stearate (m.p. 47° C.) (Myrj-52S), and ethoxylated alcohols such as polyoxyethylene (23) lauryl ester (m.p. 38°–40° C.). Specific meltable water-soluble binders are PEG 3350 and polyoxyethylene (40) stearate. The meltable water-soluble binders of use in the invention are of particular use in the preparation of tablets having increased disintegration rates in the mouth, e.g., rapid disintegration rates of less than ten seconds, for instance 1 to 5 seconds.

The meltable binder may be combined with the excipient or excipients and the pharmaceutically active agent in any sequence. The binder may be combined in dry form or in a suitable solvent such as alcohol, isopropanol or water. The dissolved binder on addition to the remaining tablet ingredients forms a wet granulation. If desired, the pharmaceutically active agent is added after drying of the wet granulation. Usually, the combined tablet ingredients are milled and mixed with a tabletting lubricant before the dry granules are compressed into tablets.

The excipients of use in the invention are generally known in the art, e.g., as described in Remington's Pharmaceutical Sciences, 18th Edition (1990), particularly pages 1633 to 1638. They impart necessary processing and compression characteristics either to the tablet formulation before tabletting, or to the finished tablet. Examples of excipients are diluents, binders, lubricants, flavors, and sweetening agents. Specific diluents of use in the invention are water soluble diluents such as mannitol, xylitol, sucrose, lactose, and sodium chloride. Suitable binders of use in the invention, in addition to the meltable binder of use in the invention, impart cohesive properties and include starch, gelatin, microcrystalline cellulose and sugars such as sucrose, glucose, dextrose, and lactose. As is clear from the above, the same excipient may be used for different purposes within the same tablet formulation.

In one embodiment of the invention, a disintegrating agent is present to increase the disintegration rate of the tablet after oral intake. Examples of disintegrating agents are cellulose such as carboxymethylcellulose, starches, clay, algins, gums and crosslinked polymers, such as crosslinked polyvinylpyrrolidone (PVP-XL).

In another embodiment of the invention, a volatilizable component is present in the tablet formation to manufacture porous tablets. After combination and compression of the tablet ingredients, the volatilizable component is removed from the tablets by heating at atmospheric or reduced pressure to form porous tablets. Suitable volatilizable components include sublimable materials such as menthol, camphor, urea, and vanillin, and materials that decompose at or below the melting point of the binder such as ammonium bicarbonate. The amount of volatilizable material ranges from about 1% to about 95% by weight, based on the weight of the combined tablet ingredients. For instance, when using ammonium bicarbonate, the amount is usually from about 50% to about 90% by weight, and when using menthol, the amount ranges from about 30% to about 55% by weight. Preferably, the volatilizable material is removed during melting step (b) according to the invention when the compressed tablets are heated above the melting point of the meltable binder for a period of time sufficient to melt the meltable binder- and to remove the volatilizable material. When using menthol, removal thereof is by heating to about 40° C. under vacuum.

The terms "porosity" and "% porous" of a tablet as used herein refer to the void spaces created by the removal of the volatilizable component of the tablet. Since removal of the volatilizable component does not affect the inner or outer dimensions of the tablet, the porosity as defined above is the percentage by weight of the volatilizable component in the original tablet formation.

In general, the melting step (b) to melt the binder in the tablet is for a period of time sufficient to melt the meltable binder. The binder solidifies after the tablets are cooled to ambient temperature. The melting and solidifying of the meltable binder in the tablet strengthens the bonding among the tablet particles by filling of the minor cracks in the tablet matrix, as shown in the scanning electron micrographs of FIGS. 1A and B.

The tablets prepared by the method of the invention may be coated with a thin layer of a coating material to improve the surface integrity of the tablet. Suitable coating materials include disaccharides such as sucrose, polysaccharides such as maltodextrins and pectin, and cellulose derivatives such as hydroxypropylmethylcellulose and hydroxypropylcellulose.

The pharmaceutically active agent of use in the invention may be any compound that is pharmaceutically active on oral intake or on rectal administration. Examples of such agents include antifungal agents such as fluconazole, pain relievers such as acetaminophen and acetylsalicylic acid, antihistamines such as diphenhydramine, doxylamine succinate and meclizine, decongestants such as pseudoephedrine hydrochloride, antibiotics such as azithromycin and erythromycin, penicillins such as sultamicillin tosylate and amoxicillin trihydrate, enzyme inhibitors such as sulbactam sodium, antihypertensives such as nifedipine, doxazosin mesylate and amlodipine besylate, antidiabetics such as glipizide, bronchodilators such as pirbuterol hydrochloride and theophylline, anti-inflammatory agents such as piroxicam and tenidap, anti-depressants such as sertraline hydrochloride, antacids such as calcium carbonate and magnesium oxide, and non-sedative antihistamines such as cetirizine. It is understood that the pharmaceutically active agents of use in the invention include nutritional and dietary supplements, for example, vitamins.

The following examples illustrate the invention. The strength of the tablets was measured with a tablet hardness tester, particularly the Schleuniger Hardness Tester, and a friability tester, particularly the Vanderkamp Friabilator. The hardness of the tablet is the force in kp (kilopond) required to break a tablet. The higher the kp value, the stronger the tablet is. Friability is the percentage of the tablet weight loss after a certain number of revolutions in the Vanderkamp Friabilator. The lower the percentage is, the stronger the tablet. As used in the Examples, the term "failed" refers to tablets which break during friability testing.

EXAMPLE 1

54.5% Porous Tablets

Tablet A: The following ingredients were blended and compressed into tablets of 0.5 inch diameter and 0.130 inch thickness. These tablets were then heated at 72° C. under vacuum for 18 hours. This temperature is above the melting point of PEG 3350, 58° C. A 54.5% porous structure was formed after the ammonium bicarbonate was removed by thermal decomposition.

| INGREDIENTS OF TABLET A | MG/TABLET |
| --- | --- |
| 1 Ammonium bicarbonate (pore former) | (300.00) later removed |
| 2 Mannitol | 168.00 |
| 3 Banana flavor | 8.00 |
| 4 Aspartame | 4.00 |
| 5 PEG 3350 | 20.00 |
| 6 PVP-XL | 40.00 |
| 7 Sodium stearyl fumarate | 10.00 |
| TOTAL | 250.00 |

Tablet B: Tablets of 0.5 inch diameter and 0.125 inch thickness were made based on the following formulation which contained no PEG 3350. The tablet size, weight, and the relative amounts (weight to weight ratios) of the non-volatilizable components (ingredients 2 to 6) remained the same as in Tablet A in order to make a fair comparison between the two tablets. The porosity of the comparative tablet was therefore maintained at 54.5%.

| INGREDIENTS OF TABLET B | MG/TABLET |
|---|---|
| 1 Ammonium bicarbonate (pore former) | (300.00) later removed |
| 2 Mannitol | 183.27 |
| 3 Banana flavor | 8.73 |
| 4 Aspartame | 4.36 |
| 6 PVP-XL | 43.64 |
| 7 Sodium stearyl fumarate | 10.00 |
| TOTAL | 250.00 |

The physical characterization of these two tablets is shown in Table 1.

TABLE 1

| | Diameter (inch) | Thickness (inch) | Hardness (kp) | Friability (%) 100 revolutions |
|---|---|---|---|---|
| Tablet A | 0.5 | 0.130 | 4.0 | 0.8 |
| Tablet B | 0.5 | 0.125 | 2.4 | 6.8 |

The tablet strength of Tablet A is much better than that of Tablet B because of the presence of melted and solidified PEG 3350.

EXAMPLE 2

38% Porous Tablets

Tablet C: The following ingredients were blended and compressed into tablets of 0.5 inch diameter and 0.114 inch thickness. These tablets were then heated at 42° C. under vacuum. A 38% porous structure was formed after the menthol was removed by sublimation.

Tablet D: These tablets were made by further heating Tablet C at 72° C. under vacuum for one hour.

| INGREDIENTS OF TABLETS C AND D | MG/TABLET |
|---|---|
| 1 Menthol (pore former) | (150) later removed |
| 2 Mannitol | 150 |
| 3 Banana flavor | 8 |
| 4 Aspartame | 4 |
| 5 PEG 3350 | 60 |
| 6 PVP-XL | 15 |
| 7 Sodium stearyl fumarate | 8 |
| TOTAL | (395) 245 |

The physical characterization of these two tablets is shown in Table 2.

TABLE 2

| | Diameter (inch) | Thickness (inch) | Hardness (kp) | Friability (%) 100 revolutions |
|---|---|---|---|---|
| Tablet C | 0.5 | 0.114 | below scale | Failed |
| Tablet D | 0.5 | 0.114 | 2.7 | 0.4 |

The improvement in both hardness and friability was dramatic with the tablets (Tablet D) that were heated above the melting point of PEG 3350 (580° C.). The amount of void space in Tablet D was not compromised by further heating and melting of PEG 3350. This is demonstrated by the microscopic views of both tablets in FIGS. 1A and B. In comparing the photographs of the two tablets, it is evident that the melted PEG 3350 had filled and connected the hairline cracks of the type visible in Tablet C.

EXAMPLE 3

54.5% Porous Tablets

Tablet E: The following ingredients were blended and compressed into tablets of 0.5 inch diameter and 0.168 inch thickness. These tablets were then heated at 40° C. under vacuum for 18 hours. A 54.5% porous structure was formed after the menthol was removed by sublimation.

Tablet F: These tablets were made by further heating Tablet E at 70° C. under vacuum for 16 hours.

| INGREDIENTS OF TABLETS E AND F | MG/TABLET |
|---|---|
| 1 Menthol (pore former) | (300) later removed |
| 2 Mannitol | 168 |
| 3 Banana flavor | 8 |
| 4 Aspartame | 4 |
| 5 PEG 3350 | 30 |
| 6 PVP-XL | 30 |
| 7 Sodium stearyl fumarate | 10 |
| TOTAL | (550) 250 |

The physical characterization of these two tablets is shown in Table 3.

TABLE 3

| | Diameter (inch) | Thickness (inch) | Hardness (kp) | Friability (%) 25 revolutions |
|---|---|---|---|---|
| Tablet E | 0.5 | 0.168 | below scale | failed |
| Tablet F | 0.5 | 0.168 | below scale | 8.5 |

The difference in friability of both tablets due to the melting and solidifying of PEG 3350 is demonstrated in FIG. 2, which is a plot of the tablet weight loss as a function of the number of revolutions in the Vanderkamp friabilator.

EXAMPLE 4

75% Porous Tablets

Tablet G: The following ingredients 1, 2, 3, 5, 6, and 7 were blended and then wet-granulated with a solution of PEG 3350 (ingredient 4) in ethanol. The dry granulates were milled and blended with sodium stearyl fumarate (ingredient 8). The final blend was compressed into tablets of 0.625 inch diameter. These tablets were then heated at 70° C. under vacuum. A 75% porous structure was formed after the ammonium bicarbonate was removed during the heating by thermal decomposition.

| INGREDIENTS OF TABLET G | MG/TABLET |
|---|---|
| 1 Ammonium bicarbonate (pore former) | (600) later removed |
| 2 Mannitol | 90 |
| 3 Avicel PH101 (microcrystalline cellulose) | 35 |
| 4 PEG 3350 | 20 |
| 5 PVP XL | 10 |

-continued

| INGREDIENTS OF TABLET G | MG/TABLET |
|---|---|
| 6 Aspartame | 15 |
| 7 Banana flavor | 15 |
| 8 Sodium stearyl fumarate | 15 |
| TOTAL | (880) 200 |

The friability of the tablets after 10 revolutions in the Vanderkamp friabilator was 4%.

EXAMPLE 5

Tablets Not Containing Volatilizable Component

Tablet H: The following ingredients were blended and compressed into tablets of 0.625 inch diameter and 0.2 inch thickness.

Tablet I: These tablets were made by heating tablet H at 70° C. for 3 hours. These tablets remained non-porous in the absence of a volatilizable component.

| INGREDIENTS OF TABLETS H AND I | MG/TABLET |
|---|---|
| 1 Lactose | 733.33 |
| 2 PEG 3360 | 129.4 |
| 3 Sodium stearyl fumarate | 17.27 |
| TOTAL | 880 |

The physical characterization of these two tablets is shown in Table 4.

TABLE 4

| | Diameter (inch) | Thickness (inch) | Hardness (kP) | Friability (%) 100 revolutions |
|---|---|---|---|---|
| Tablet H | 5/8 | 0.2 | 3.5 | failed after 20 rev. |
| Tablet I | 5/8 | 0.2 | 3.5 | 0.5 |

The friability of Tablet I was improved because of the melting and then solidifying of PEG 3350.

EXAMPLE 6

36% Porous Tablets

Tablet J: The following ingredients were blended and compressed into tablets of 0.5 inch diameter and 0.125 inch thickness. These tablets were then heated at 40° C. under vacuum for 18 hours. A 36% porous structure was formed after the menthol was removed by sublimation.

Tablet K: These tablets were made by further heating Tablet J at 70° C. under vacuum for 4 hours.

| INGREDIENTS OF TABLETS J AND K | MG/TABLET |
|---|---|
| 1 Menthol (pore former) | (150) later removed |
| 2 Mannitol | 150 |
| 3 PVP-XL | 15 |
| 4 Myrj-52S | 60 |
| 5 Piroxicam | 20 |
| 6 Banana flavor | 8 |
| 7 Aspartame | 4 |
| 8 Sodium stearyl fumarate | 8 |

-continued

| INGREDIENTS OF TABLETS J AND K | MG/TABLET |
|---|---|
| TOTAL | (415) 265 |

The physical characterization of these two tablets is shown in Table 5.

TABLE 5

| | Diameter (inch) | Thickness (inch) | Hardness (kp) | Friability (%) 80 revolutions |
|---|---|---|---|---|
| Tablet J | 0.5 | 0.125 | below scale | Failed after 20 rev. |
| Table K | 0.5 | 0.125 | 2 kp | 0.0 |

Both hardness and friability of Tablet K were improved because of the melting and solidifying of Myrj-52S.

EXAMPLE 7

75% Porous Tablets

Tablet L: The following ingredients 1, 2, 3, 4, 8 and 9 were blended and then wet-granulated with a solution of ingredients 5 and 6 in isopropanol. The dry granules were milled and blended with ingredient 7. Finally, ingredient 10 was mixed with the blend. The final blend was compressed into tablets of 0.625 inch diameter. These tablets were then heated at 65° C. under vacuum for 18 hours to remove ammonium bicarbonate by thermal decomposition. A 75% porous structure was formed.

| INGREDIENTS OF TABLET L | MG/TABLET |
|---|---|
| 1 Ammonium bicarbonate (pore former) | (600) later removed |
| 2 Mannitol | 29 |
| 3 PVP-XL | 10 |
| 4 Avicel PH 105 | 35 |
| 5 PEG 3350 | 5 |
| 6 Klucel EF | 5 |
| 7 Microencapsulated fluconazole | 71 |
| 8 Banana flavor | 15 |
| 9 Aspartame | 15 |
| 10 Sodium stearyl fumarate | 15 |
| TOTAL | (800) 200 |

The friability of Tablet L was 0 0% after 10 revolutions in the Vanderkamp friabilator.

EXAMPLE 8

Tablets Not Containing Volatilizable Component

Tablet M: The following ingredients were blended and compressed into tablets of 0.5 inch diameter and 0.104 inch thickness.

Tablet N: These tablets were made by further heating Tablet M at 83° C. for one hour.

| INGREDIENTS OF TABLETS M AND N | MG/TABLET |
|---|---|
| 1 Xylitol | 322 |
| 2 Carnauba wax | 40 |
| 3 Doxylamine succinate | 25 |

-continued

| INGREDIENTS OF TABLETS M AND N | MG/TABLET |
|---|---|
| 4 Grape flavor | 5 |
| 5 Magnesium stearate | 8 |
| TOTAL | 400 |

The physical characterization of these two tablets is shown in Table 6.

TABLE 6

| | Diameter (inch) | Thickness (inch) | Hardness (kp) | Friability (%) 100 revolutions |
|---|---|---|---|---|
| Tablet M | 0.5 | 0.104 | 3 kp | 0.96 |
| Tablet N | 0.5 | 0.104 | 8 kp | 0.00 |

Both hardness and friability of Tablet N were improved because of the melting and solidifying of carnauba wax.

EXAMPLE 9

Tablets Not Containing Volatilizable Component

Tablet O: The following ingredients were blended and compressed into tablets of 0.5 inch diameter and 0.090 inch thickness.

Tablet P: These tablets were made further heating Tablet M at 60° C. for one hour.

| INGREDIENTS OF TABLETS M AND N | MG/TABLET |
|---|---|
| 1 Lactose | 241.4 |
| 2 PEG 3350 | 40 |
| 3 Tenidap | 90.6 |
| 4 Explotab (sodium starch glycolate) | 20 |
| 5 Magnesium stearate | 8 |
| TOTAL | 400 |

The physical characterization of these two tablets is shown in Table 7.

TABLE 7

| | Diameter (inch) | Thickness (inch) | Hardness (kp) | Friability (%) 100 revolutions |
|---|---|---|---|---|
| Tablet O | 0.5 | 0.104 | 3 kp | failed at 10 rev |
| Tablet P | 0.5 | 0.104 | 8 kp | 0.02 |

Both hardness and friability of Tablet K were improved because of the melting and solidifying of PEG 3350.

I claim:

1. A tablet of increased strength made according to a method for the preparation thereof which comprises the steps of (a) combining and compressing a water soluble meltable binder, at least one excipient and a pharmaceutically active agent into a tablet wherein said pharmaceutically active agent is fluconazole, piroxicam, tenidap or doxylamine succinate, (b) melting said binder in said tablet, and (c) solidifying said binder.

2. A tablet according to claim 1 wherein said binder is polyethylene glycol, a sucrose ester, an ethoxylated fatty acid, or an ethoxylated alcohol.

3. A tablet according to claim 1 wherein said binder has a melting point ranging from about 20° C. to about 100° C.

4. A tablet according to claim 1 wherein step (a) includes combining with a volatilizable material which is removed after said compressing step.

5. A tablet according to claim 4 wherein said volatilizable material is ammonium bicarbonate.

6. A porous tablet when made according to the method of claim 4.

7. A tablet according to claim 6 having a porosity of 50% to 90%.

* * * * *